(12) United States Patent
Sun

(10) Patent No.: US 7,041,253 B1
(45) Date of Patent: May 9, 2006

(54) SAMPLE COLLECTION AND TEST DEVICE

(75) Inventor: Ming Sun, Cherry Hill, NJ (US)

(73) Assignee: Sun Biomedical Laboratories, Inc., Blackwood, NJ (US)

( * ) Notice: Subject to any disclaimer, the term of this patent is extended or adjusted under 35 U.S.C. 154(b) by 551 days.

(21) Appl. No.: 10/201,460

(22) Filed: Jul. 23, 2002

(51) Int. Cl.
  *G01N 33/00* (2006.01)

(52) U.S. Cl. .......................... 422/58; 422/55; 422/56; 422/68.1; 422/99; 422/102; 422/104

(58) Field of Classification Search .................. 422/50, 422/55, 56, 57, 58, 61, 68.1, 82.1, 99, 100, 422/101, 102, 104; 600/584; 435/810, 975
See application file for complete search history.

(56) References Cited

U.S. PATENT DOCUMENTS

| | | | |
|---|---|---|---|
| 3,849,256 A | 11/1974 | Linder | |
| 4,237,234 A | 12/1980 | Meunier | |
| 4,473,530 A | 9/1984 | Villa-Real | |
| 4,518,565 A | 5/1985 | Boger et al. | |
| 4,744,952 A * | 5/1988 | Ogita | 422/56 |
| 4,976,923 A | 12/1990 | Lipsky et al. | |
| 5,119,830 A | 6/1992 | Davis | |
| 5,149,505 A | 9/1992 | English et al. | |
| 5,403,551 A | 4/1995 | Galloway et al. | |
| 5,501,837 A | 3/1996 | Sayles | |
| 5,591,401 A | 1/1997 | Sayles | |
| 5,640,969 A | 6/1997 | Davis | |
| 5,916,815 A * | 6/1999 | Lappe | 436/92 |

* cited by examiner

Primary Examiner—Yelena Gakh
Assistant Examiner—Sam P. Siefke
(74) Attorney, Agent, or Firm—Norman E. Lehrer

(57) ABSTRACT

A sample collection and test device that includes a container adapted to hold a fluid test sample, a lid secured to the container, a plate with a plurality of grooves and within each groove a test strip may be held, and a mechanism for securing the plate to the lid where the plate is able to pivot from a secured, inactive position within the lid to an active position within the container where the test strips contact the test sample is disclosed. Either the container or the lid may include a window in order to view the reactions on the test strips.

11 Claims, 4 Drawing Sheets

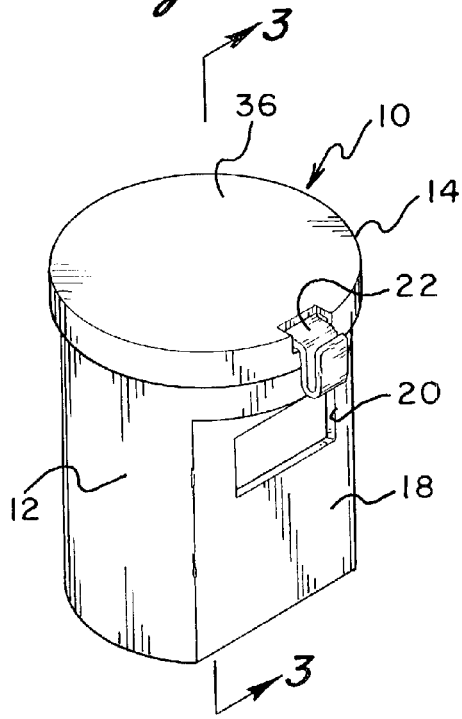
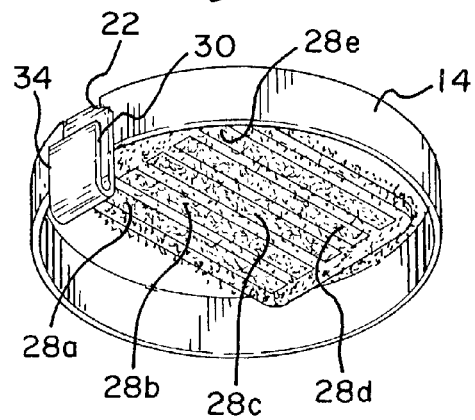
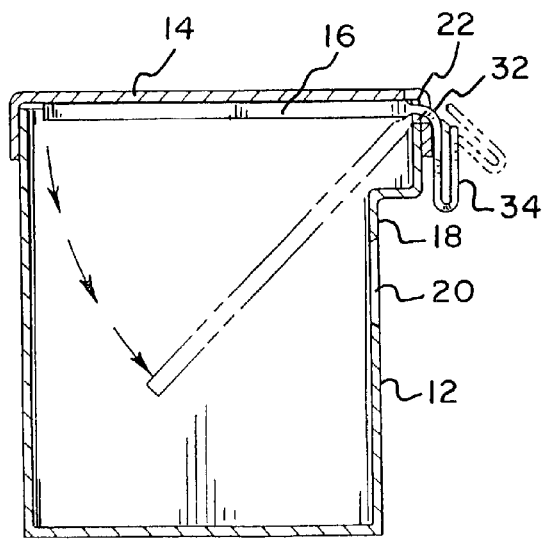
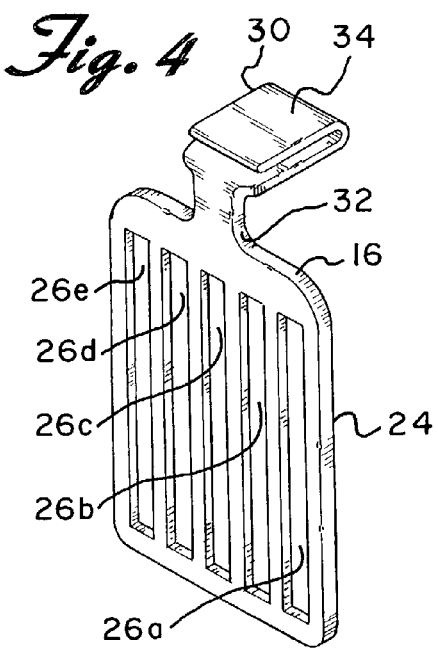

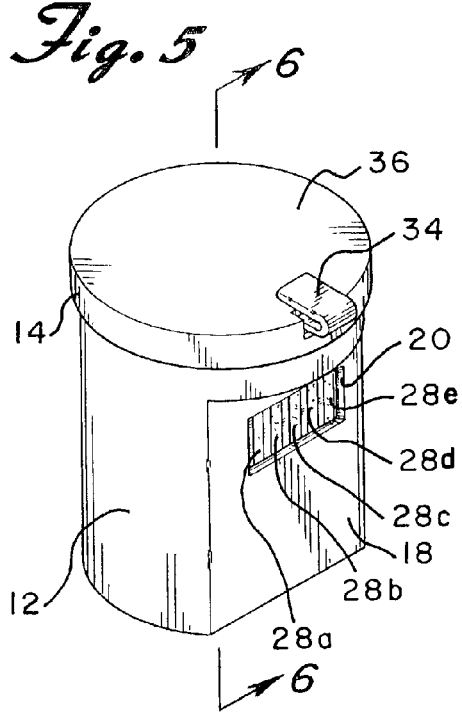
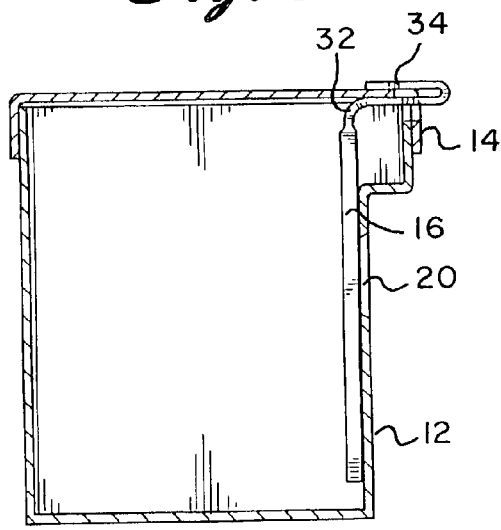
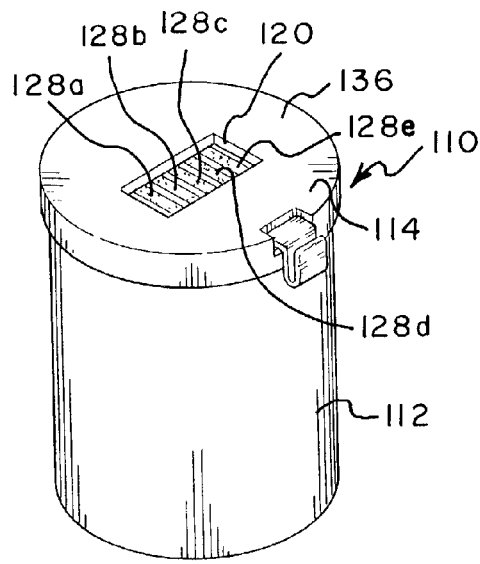
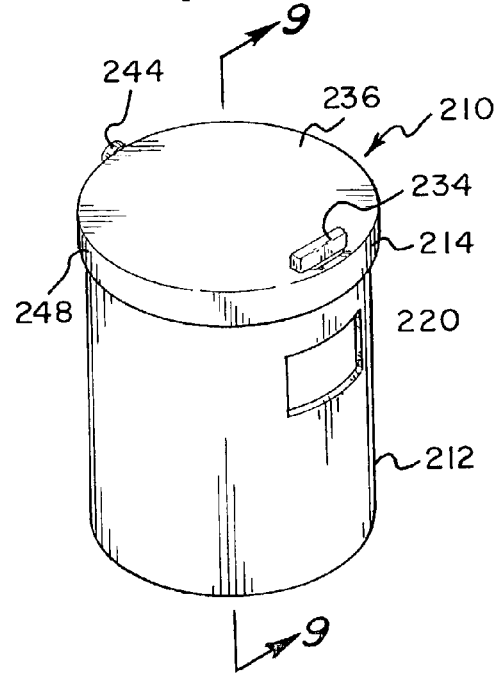

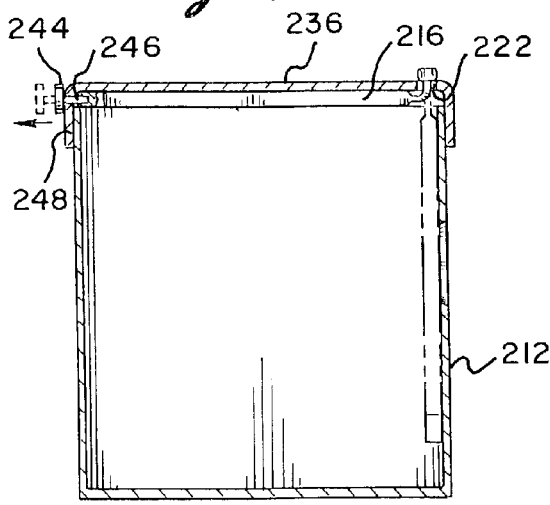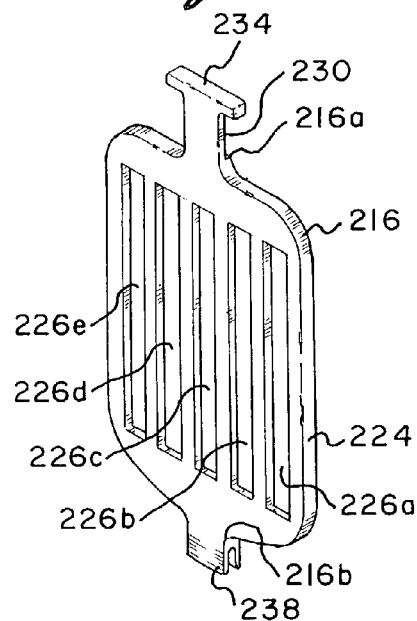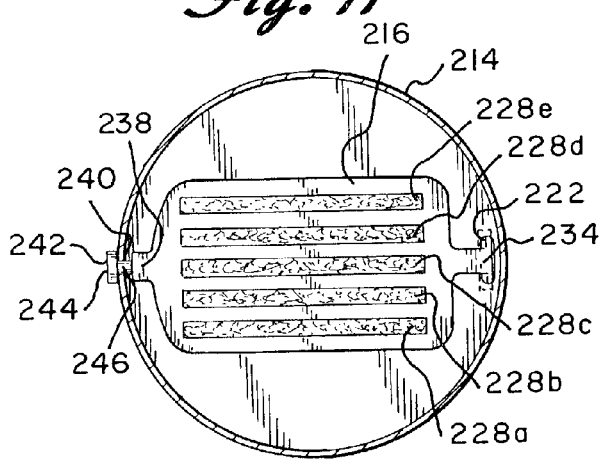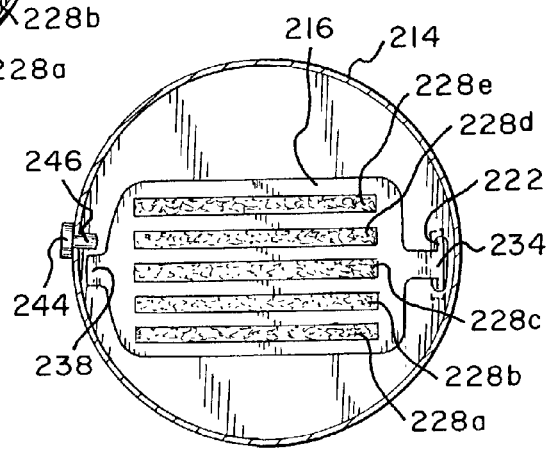

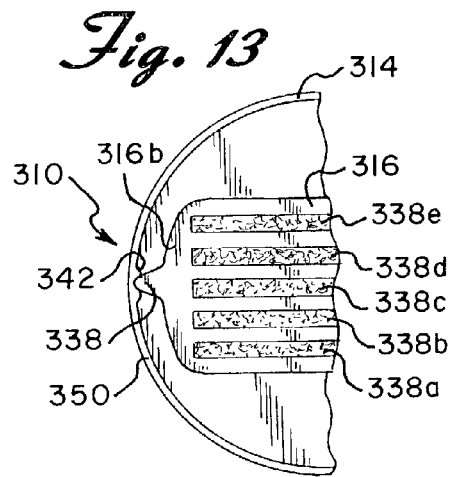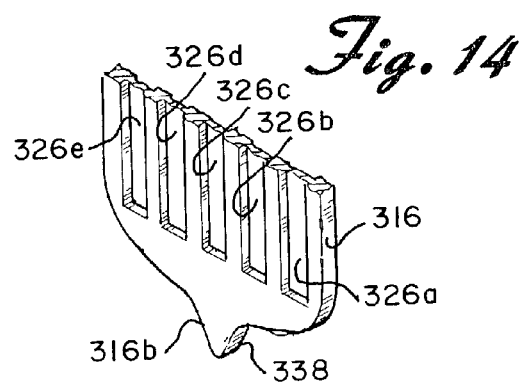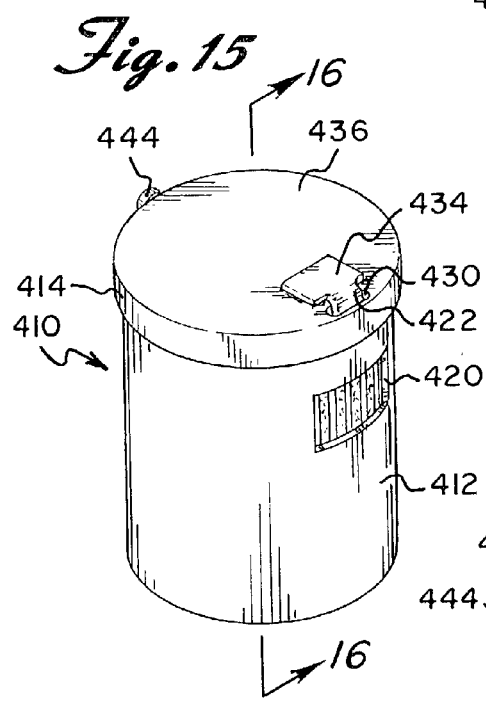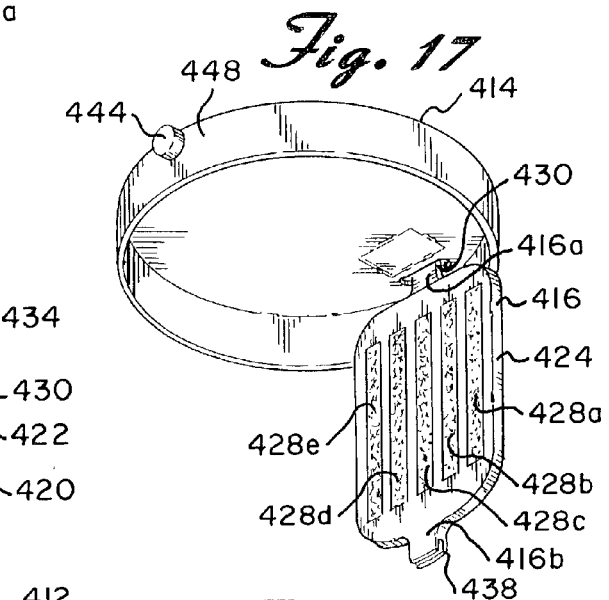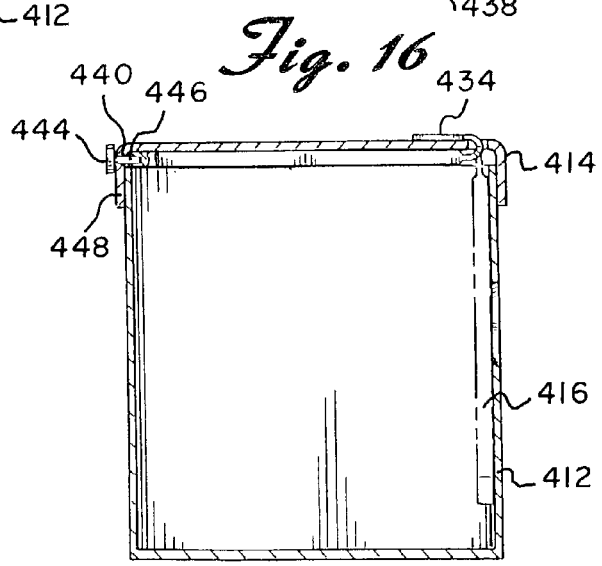

SAMPLE COLLECTION AND TEST DEVICE

BACKGROUND OF THE INVENTION

The present invention is directed toward an immunoassay test device and more particularly, toward a test device incorporating test strips in the cap of a test sample container.

Fluid test samples, for example urine or other bodily fluids, are often collected in containers or cups with lids. When a test is to be run on the sample, the lid is either punctured, removed, or otherwise penetrated in order to remove the fluid therefrom to a test device. The problem with this type of collection device is that the likelihood of the test sample spilling and contaminating the user is very high.

Another type of test device involves placing a test strip with test reagents contained therein directly into the test sample. Again, the risk of contamination is high. In this test, however, it is the test sample that can be contaminated. Thus, the test results may be inaccurate. Another problem with this type of device is that the test strip may become saturated to the point where the test strip cannot be read.

Some patents have addressed the problems discussed above and have proposed solutions. For example, U.S. Pat. No. 5,403,551 to Galloway discloses a container with a front wall that includes a plurality of test strips. A series of passageways in the device allows liquid within the container to wet a portion of the test strips when the container is inverted in order to perform an analysis. With this device, however, there is a possibility of leakage when the container is inverted, thereby leading to possible contamination. Furthermore, the test strip may be saturated too much or not enough, thereby leading to inaccurate test results.

U.S. Pat. No. 5,119,830 to Davis discloses an analytical specimen cup that houses a test sample. A testing means includes a cup and a lid. The lid includes a number of test strips for providing a visual indication of a variety of different test results. The lid is secured to the container. In order to use the device, the container is tilted so that the test sample enters a portion of the lid and activates the test. Again, this device requires that the container be tilted in order for the sample to contact the test strips. Thus, there is a possibility of contamination and inaccurate results as discussed above.

Likewise, U.S. Pat. No. 4,976,923 to Lipsky et al. discloses a fluid test apparatus that includes a container and a cover. The cover is screwed onto the container. The cover contains reagents and holes through which the test sample reaches the reagents when the container is inverted.

Therefore, a need exists for test sample collection device that allows for a test to be conducted within the collection device without having to transfer the test sample and that allows the test to be conducted without having to invert or otherwise disturb the container of the collection device.

SUMMARY OF THE INVENTION

The present invention is designed to overcome the deficiencies of the prior art discussed above. It is an object of the present invention to provide a sample collection and test device that includes a container and a lid where test strips are located within the lid of the device.

It is another object of the present invention to provide a sample collection and test device that avoids the test sample from leaking from the device.

It is a further object of the present invention to provide a sample collection and test device that allows a test to be conducted without having to invert or otherwise disturb the container of the device.

In accordance with the illustrative embodiments demonstrating features and advantages of the present invention, there is provided a sample collection and test device that essentially includes a container adapted to hold a fluid test sample, a lid secured to the container, a plate with a plurality of grooves and within each groove a test strip may be held, and means for securing the plate to the lid where the plate is able to pivot from a secured, inactive position within the lid to an active position within the container where the test strips contact the test sample. In one embodiment the container may include a window in order to view the reactions on the test strips. In another embodiment the window may be located on the top of the lid. The securing means may take different forms. For example, in one embodiment the securing means may include a handle extending from the plate and a clip attached to the handle. An opening is formed within the lid so that the clip may be mounted within the opening. In another embodiment the securing means may include the plate having a handle at one end with an elongated flexible flange extending from the handle, a clip located at the opposite end of the plate, and a slot formed through the lid and through which slot the handle and flange extend. The lid has an opening in the side thereof and a pin member with a neck portion and a head, the neck portion extends through the opening and the clip is releasably secured onto the neck portion. In a further embodiment the flange may be in the form of a square. The securing means may also be in the form of the plate having a pointed end and the interior of the lid having a contoured portion into which the pointed end releasably fits.

Other objects, features, and advantages of the invention will be readily apparent from the following detailed description of preferred embodiments thereof taken in conjunction with the drawings.

BRIEF DESCRIPTION OF THE DRAWINGS

For the purpose of illustrating the invention, there is shown in the accompanying drawings forms which are presently preferred; it being understood that the invention is not intended to be limited to the precise arrangements and instrumentalities shown.

FIG. 1 is a front perspective view of a first embodiment of the test device of the present invention with the test strip holding plate held within the cap of the device;

FIG. 2 is a bottom perspective view of the cap of the test device of the present invention;

FIG. 3 is a cross-sectional view taken through line 3—3 of FIG. 1;

FIG. 4 is a front perspective view of a test strip holding plate of the test device of the present invention;

FIG. 5 is a front perspective view of the test device of the present invention with the test strip holding plate in a vertical position so as to be seen through the viewing window of the test cup;

FIG. 6 is a cross-sectional view taken through line 6—6 of FIG. 5;

FIG. 7 is a front perspective view of a second embodiment of the present invention with a viewing window located in the top of the cap;

FIG. 8 is a front perspective view of a third embodiment of the present invention with a viewing window located along the side of the cup of the test device;

FIG. 9 is a cross-sectional view taken through line 9—9 of FIG. 8;

FIG. 10 is a front perspective view of a test strip holding plate of the third embodiment of the present invention;

FIG. 11 is a bottom plan view of cap of the test device of the third embodiment of the present invention with the test strip holding plate secured therein;

FIG. 12 is a bottom plan view of the cap of the test device of the third embodiment of the present invention with the test strip holding plate being released therefrom;

FIG. 13 is a partial bottom plan view of the cap with a test strip holding plate secured therein of the fourth embodiment of the test device of the present invention;

FIG. 14 is a partial front perspective view of a test strip holding plate of the fourth embodiment of the test device of the present invention;

FIG. 15 is a front perspective view of a fifth embodiment of the present invention;

FIG. 16 is a cross-sectional view taken through line 16—16 of FIG. 15; and FIG. 17 is a bottom perspective view of the cap with the test strip holding plate in a vertical position of the test device of the fifth embodiment of the present invention.

DETAILED DESCRIPTION OF THE PREFERRED EMBODIMENTS

Referring now to the drawings in detail wherein like reference numerals have been used throughout the various figures to designate like elements, there is shown in FIG. 1 a test device constructed in accordance with the principles of the present invention and designated generally as 10.

A first embodiment of the present invention is shown in FIGS. 1–6. The test device includes a generally circular container or cup 12, a cap or lid 14, and a flexible test strip holding plate 16. The cup 12 has a cut-out portion 18 with a window 20 located therein. The cut-out portion 18 prevents the cup 12 from rolling if the cup 12 is turned on its side and, as will be seen, allows for better viewing of the test strips. The cap 14 has an opening 22. The cap 14 may be snap fit onto the cup 12. Other means well known and used in the art may also be used, for example, screw threads. The test strip holding plate 16 includes a generally flat, rectangular portion 24 with a plurality of grooves 26a–26e, for example extending there along on both sides of the plate 16. (See FIG. 4.) A test strip 28a–28e, for example, may be held within each groove. The holding plate 16 also has a handle 30 with a curved portion 32. The end of the handle 30 is in the form of a clip 34, the purpose of which will be described below.

The plate 16 fits or is secured within the cap 14 so that the handle 30 extends through the opening 22 of the lid 14. The plate 16 fits within the cap 14 so that it is mounted within the opening 22 and may pivot between a substantially horizontal, inactive position (see FIG. 2) and a substantially vertical, active position (see FIG. 6.) When the plate 16 is in a vertical position the clip 34 of the handle 30 is secured onto the top 36 of the cap 14. When the plate 16 is in a vertical position it can be seen through the window 20 of the cup 12. (See FIG. 5.)

In order to use the test device the plate 16 is held in a horizontal position within the cap 14. The cap 14 is then removed and the cup 12 is filled with a test sample. The cap 14 is then secured onto the cup 12. The clip 34 of the plate 16 is grasped and is secured into the top 36 of the cap 14, thereby allowing the plate 16 to pivot into its operative position within the cup 12. (See FIG. 3.) The fluid contacts the plate 16 and the test strips therein so that the sample is wicked up the strips and any reaction may be viewed through the window 20.

A second embodiment of the test device 110 is shown in FIG. 7. In this embodiment the test device essentially functions in the same manner as described in the first embodiment with the modifications noted below.

The cup 112 is substantially the same as the cup in the first embodiment; however, the cup 112 in this embodiment does not have a cut-out portion. Also, the viewing window 120 is located in the top 136 of the cap 114 rather than along the side of the cup as in the first embodiment. Accordingly, the test strip plate must be in the horizontal position rather than in the vertical position in order to view reactions on the test strips 128a–128e.

In order to use the device, cap 114 is removed and the cup 112 is filled with a test sample. The cap 114 is then secured onto the cup 112. The clip of the plate is grasped and is secured into the top 136 of the cap 114, thereby allowing the plate to pivot into its operative position within the cup 112. The fluid contacts the plate and the test strips therein so that the sample is wicked up the strips. The plate is then raised and held against the underside of the cap 114 so that any reactions may be viewed through the window 120.

A third embodiment of the test device 210 is shown in FIGS. 8-12. In this embodiment the cup 212 is generally circular with a viewing window 220 located along a side thereof. (See FIG. 8.) The plate 216 includes a generally flat portion 224 with a plurality of grooves 226a–226e extending there along as described in the other embodiments. (See FIG. 10.) Test strips 228a–228e, for example, may be held within the grooves 226a–226e. Located at one end 216a of the holding plate 216 is a handle portion 230 with an elongated flange 234 extending therefrom. The handle portion 230 can be bent but has plastic memory thereby normally biasing the plate 218 downwardly into a vertical position. Located at the opposite end 216b of the holding plate 216 is a clip member 238.

The top 236 of the lid 214 has a slot 222 located therethrough. Located across from the end of the lid with the slot 222 is an opening 240 through which retaining means, such as pin member 242 is inserted. The pin member 242 includes a head 244 and an elongated, generally cylindrical neck portion 246 extending therefrom. (See FIG. 12.) The pin member 242 fits into opening 240 of the lid 214 so that the head 244 abuts the outer side 248 of the lid 214 and the neck portion 246 extends inwardly, into the interior of the test device.

The test strip holding plate 216 fits or is secured within the lid 214 of the test device. (See FIG. 11.) Specifically, the flange 234 of the plate 216 extends through the slot 222 in the lid 214. The length of the flange 234 is greater than the diameter of the slot 222 so that once the flange 234 has passed through the slot 222, it is secured therein with the handle 230 extending through the slot 222 and the flange 234 resting on the top 236 of the lid 214. The clip 238 slidably fits or is releasably mounted onto or catches the neck portion 246 of the pin member 242. In an inoperative position, the plate 216 is held within the lid 214 as shown in FIG. 11 with the clip member 238 held in place on the neck portion 246 of the pin member 242 and the handle portion 230 bent upwardly.

In order to use the plate 216 and the tests strips 228a–228e located therein, the user releases the clip member 238 from the neck portion 246 by pulling the pin member 242 outwardly. (See FIG. 9.) This action causes the clip member 238 to slide off of the neck portion 246 and into the cup 212. (See FIG. 12.) Because the handle portion 230 is biased downwardly, it will naturally fall into a vertical position within the cup 212. The test strips housed in the holding plate 216 are now in a generally vertical position and can contact the test sample collected therein. (See FIG. 9.)

A fourth embodiment of the test device 310 is shown in FIGS. 13 and 14. In this embodiment, the test device functions in the same manner as described in the third embodiment. The structure in this embodiment differs in the mechanism for securing or attaching the test strip holding plate 316 with its plurality of grooves 326a–326e having test strips 328a–328e located therein to the lid 314. That is, instead of the clip member 238 as described in the embodiment above, in this embodiment the end of the plate 316b comes to a point 338. Instead of a pin member secured to the lid, there is a contoured portion 342 within the inside surface 350 of the side of the lid 314 and into which the pointed end 338 fits. As in the third embodiment, the plate 316 may be released from the lid 314 by flexing or pushing down on the lid 314 after it is screwed onto the cup 312. This action causes the pointed end 338 of the plate 316 to be released from the contoured portion 342 of the lid 314.

A fifth embodiment of the test device 410 of the present invention is shown in FIGS. 15–17. This embodiment includes a generally circular cup 412 with a viewing window 420 located along a side thereof. (See FIG. 15.) The plate 416 includes a generally flat portion 424 with a plurality of grooves extending there along as described in the other embodiments. (See FIG. 17.) Test strips 428a–428e, for example, may be held within each of the grooves. Located at one end 416a of the holding plate 416 is a handle portion 430 with a flat, generally square, flexible flange 434 extending therefrom. The handle portion 430 has plastic memory and is normally biased downwardly. Located at the opposite end 416b of the holding plate 416 is a clip member 438.

The top 436 of the lid 414 has a slot 422 located therethrough. Located across from the end of the lid with the slot 422 is an opening 440 through which a pin member 442 is inserted. The pin member 442 includes a head 444 and an elongated, generally cylindrical neck portion 446 extending therefrom. (See FIG. 16.) The pin member 442 fits into the side of the lid so that the head 444 abuts the outer side 448 of the lid 414 and the neck portion 446 extends inwardly, into the interior of the test device.

The test strip holding plate 416 is secured to or fits within the lid 414 of the test device. Specifically, the flange 434 of the plate 416 extends through the slot 422 in the lid 414. (See FIG. 15.) The width of the flange 434 is greater than the diameter of the slot 422 so that once the flange 434 has passed through the slot 422, it is secured therein with the handle 430 extending through the slot 422 and the flange 434 resting on top 436 of the lid 414. The clip member 438 slidably fits or is releasably mounted onto or catches the neck portion 446 of the pin member 442. In an inoperative position, the plate 416 is held within the lid 414 with the clip member 438 held in place on the neck portion 446 of the pin member 442 and handle portion 430 bent upwardly.

In order to use the plate 416 and the tests strips 428a–428e located therein, the user releases the clip member 438 from the neck portion 446 by pulling pin member 442 outwardly as discussed in previous embodiments. This action causes the clip member 438 to slide off of the neck portion 446 and into the cup 412. Because the handle portion 430 is biased downwardly, it will naturally fall into a vertical position within the cup 412. The test strips housed in the holding plate 416 are now in a generally vertical position and can contact the test sample collected therein. (See FIG. 16.)

In all of the embodiments described above, the test strips may be immunoassay test strips of the type described in Applicant's U.S. Pat. No. 6,372,516. However, almost any type of test strip may be used. The test strip may be used to analyze any type of substance as well. For example, the test device may be used to test for the presence of particular drugs in saliva, urine, or other body fluids.

The present invention may be embodied in other specific forms without departing from the spirit or essential attributes thereof and accordingly, reference should be made to the appended claims rather than to the foregoing specification as indicating the scope of the invention.

I claim:

1. A sample collection and test device comprising:
   a container adapted to hold a fluid test sample and a lid secured to said container;
   a plate adapted to hold a plurality of test strips; and
   means for securing said plate to said lid wherein said securing means includes a handle extending from said plate, the end of said handle having a clip and an opening formed within said lid, said clip being mounted within said opening and said plate pivots from a secured, inactive position within said lid to an active position within said container where the test strips contact the test sample, said plate being capable of being pivoted from said inactive position to said active position while said lid is secured to said container.

2. The sample collection and test device of claim 1 wherein said container includes a window.

3. The sample collection and test device of claim 1 wherein said lid includes a window.

4. The sample collection and test device of claim 1 wherein said plate includes a generally rectangular, flat portion with a plurality of grooves located therein.

5. The sample collection and test device of claim 1 wherein said container has a cut-out portion.

6. A sample collection and test device comprising:
   a container adapted to hold a fluid test sample and a lid secured to said container;
   a plate adapted to hold a plurality of test strips; and
   means for securing said plate to said lid wherein said plate pivots from a secured, inactive position within said lid to an active position within said container where the test strips contact the test sample, said plate being capable of being pivoted from said inactive position to said active position while said lid is secured to said container and one end of said plate has a handle with a flexible flange extending from said handle and a clip located at an opposite end of said plate.

7. The sample collection and test device of claim 6 wherein said securing means includes said lid having a slot formed therethrough and said handle and flange being adapted to extend through said slot.

8. The sample collection and test device of claim 7 wherein said securing means further includes said lid having an opening through a side thereof and a pin member with a neck portion and a head, said neck portion extending through said opening and into said container, and said clip being releasably secured onto said neck portion.

9. The sample collection and test device of claim 6 wherein said flange is elongated and is adapted to rest on the top of said lid.

10. The sample collection and test device of claim 6 wherein said flange is generally square and is adapted to rest on the top of said lid.

11. The sample collection and test device of claim 6 wherein said plate includes a generally rectangular, flat portion with a plurality of grooves located therein.

* * * * *